United States Patent [19]

McNeil

[11] Patent Number: 5,368,822
[45] Date of Patent: Nov. 29, 1994

[54] VENT SCENT ADAPTER

[76] Inventor: William S. McNeil, 7694 Belgrave Cove, Germantown, Tenn. 38138

[21] Appl. No.: 102,188

[22] Filed: Aug. 5, 1993

[51] Int. Cl.5 .............................. A61L 9/12
[52] U.S. Cl. ........................ 422/124; 239/54; 239/57; 239/58; 239/59; 239/60; 422/5; 422/122; 422/123; 422/305
[58] Field of Search .......... 422/5, 122, 123, 124, 422/305, 306; 239/54, 57, 58, 59, 60

[56] References Cited

U.S. PATENT DOCUMENTS

| | | |
|---|---|---|
| 3,423,022 | 1/1969 | Varley . |
| 3,844,478 | 10/1974 | Davis . |
| 3,908,905 | 9/1975 | von Philipp et al. . |
| 4,065,262 | 12/1977 | Petroff . |
| 4,220,281 | 9/1980 | Martens, III et al. ............. 239/59 |
| 4,493,011 | 1/1985 | Spector ............................ 422/5 |
| 4,523,870 | 6/1985 | Spector . |
| 4,604,114 | 8/1986 | Ward . |
| 4,840,773 | 6/1989 | Wade . |
| 4,903,584 | 2/1990 | Styles . |
| 5,087,273 | 2/1992 | Ward . |
| 5,141,707 | 8/1992 | Brite ................................. 422/124 |

OTHER PUBLICATIONS

Coupon/Advertisement from Washington Post—Jul. 1993, Glade "Clip-Ons".

Primary Examiner—Timothy M. McMahon
Attorney, Agent, or Firm—Edwin E. Greigg; Ronald E. Greigg

[57] ABSTRACT

A scent device including a housing having a front face with vents therein and a support on a backside for securing the housing to a vent of a blower system. A fragrance block that has passages therethrough is inserted into the housing so that air from the blower system passes through the fragrance block and out through the vents in the housing.

13 Claims, 1 Drawing Sheet

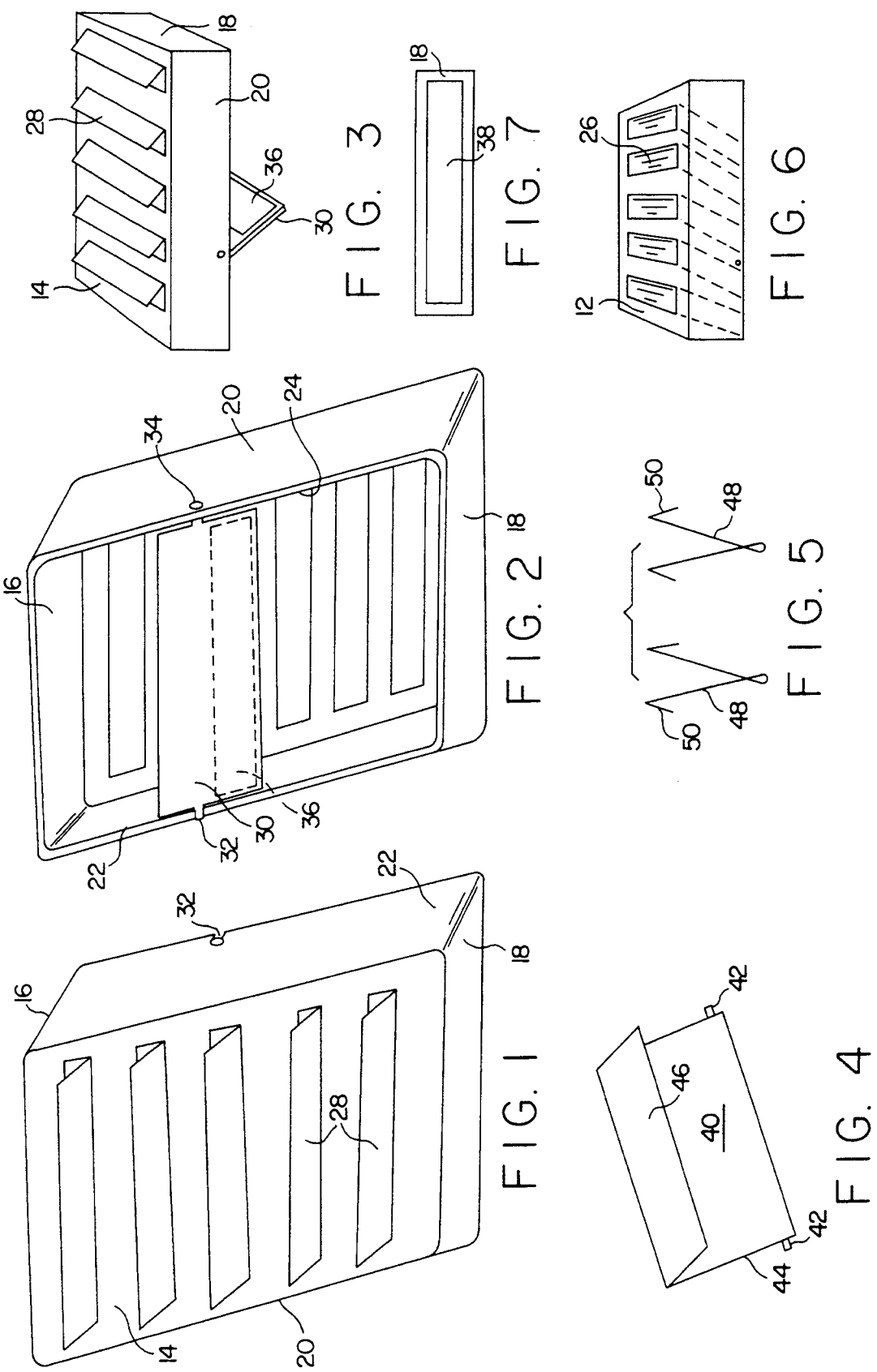

VENT SCENT ADAPTER

BACKGROUND OF THE INVENTION

This invention is directed to a deodorizing scent adapter which may be applied to a metal or plastic louvered vent in a room of a house having a a central heating or air conditioner system. In additional, it could be made to stand alone or be secured to a metal or plastic object.

Heretofore, prior art devices have been used for different aromatic scents in a room, an automobile or throughout a house. Furthermore, different scents have been added to a furnace or air conditioner filter such that the air flow from the furnace or air conditioner will blow through the filter and as such, force the scent from the filter out through the different outlet vents of different rooms provided for the furnace or air conditioner. Different types of filters and materials have been used for such purposes. One such scent is a sponge type of material which has been saturated with a liquid deodorizer and then added to a normal filter of a furnace or air conditioner. Thus, when the blower is activated, the scent will be blown through each of the outlet vents of the house. Therefore, only one scent will be throughout the house. The disadvantages of such a system is as follows:

A. Locating and opening the furnace is a job some consider beyond their knowledge.

B. Upon removing the filter to attach the sponge material, one may find a need to replace the filter and may not be prepared at that time.

C. Old furnace filters may be dirty.

D. Removing the filter may require climbing into an attic or other dusty area.

E. Many female purchasers may not know where the furnace is or how to remove a filter to attach the scented material, especially with the large numbers of female heads of households.

F. When activated, the same fragrance is circulated throughout the entire home.

Scent packages having different fragrances are available and can be used in local areas of a home for applying different scents in different areas. There is no way to circulate such fragrances. Some scent devices have made use of an electrical heating and/or blower device which requires the use of an available electrical plug which is not always readily available in the area in which one desires to add fragrance.

The present invention overcomes the adversities of the prior art and provides a simple scent package which can be secured to an outlet vent of a central heat or air conditioner system or to a main return vent. In securing the scent package to an outlet vent, different fragrances can be directed into each different room. Thus, any desired fragrance can be added to each room. Not only can the scent package be applied to outlet and inlet vents in a furnace system, the scent package can be attached to any metal or plastic object such as a stove, refrigerator, washer, dryer, or any other metal or plastic object. Also, the scent package will stand alone upon any desired object to provide a local fragrance. Obviously, when the scent package is secured to a central heat or air conditioner room vent, the fragrance will permeate the room each time the unit operates.

OBJECT AND SUMMARY OF THE INVENTION

It is therefore an object of applicant's invention to provide a simple, readily applicable and removable scent device which can be used by anyone in a home or office and in any room in which a fragrance of a particular type is desired to be used.

The major advantages of the scent package of the present invention are as follows:

A. It is easy to install,

B. It does not require an electrical outlet,

C. No special knowledge or skill is required for installation,

D. By utilizing the different outlet vents of a heater or air conditioner system, any desired fragrance can be directed into any desired room, and E. A fragrance need not be directed into any room in which it is not desired.

The invention will be better understood and further objects and advantages thereof will become more apparent from the ensuing detailed description of a preferred embodiment taken in conjunction with the drawings.

BRIEF DESCRIPTION OF DRAWINGS

FIG. 1 is a front perspective view illustrating the front and one side of the scent package;

FIG. 2 is a rear perspective view illustrating the rear of the device;

FIG. 3 is a side perspective view which illustrates a rotatable plate—magnet which is used to attach the scent package to a metal vent;

FIG. 4 illustrates a different type hanger which is formed of a plastic material;

FIG. 5 illustrates spring type hangers;

FIG. 6 illustrates a fragrance block which can be inserted into the scent package; and FIG. 7 illustrates a side view of another embodiment of the scent package showing an opening for insertion of a scent block.

Referring to the drawings, there is shown in the drawings a scent package into which a scent block 12 of any particular fragrance can be inserted for use with an outlet vent of a blower device, not shown. As shown, the scent device is made like a rectangular or square box having a front side 14, upper and lower ends 16, 18, left side 20, right side 22, and an open rear 24. In one embodiment an aperture is provided in one side of the scent device so that a fragrance block 12 may be inserted into the open side. The fragrance block is shown with angular passages 26 through which air from a vent blows. The slots in the fragrance block are in alignment with the louvers of an outlet vent of the blower system and likewise are in alignment with the vents in the front face of the scent device. Thus, if the vent openings of the blower system are angled up, the passages in the fragrance block and vents in the scent device will be up. In this way, the air from the blower system will incur the least resistance passing through the scent device. As the air blows through the fragrance block, the fragrance is collected by the air and is carried by the air through air opening slots 28 in the front face of the scent device. In the rear side of the scent device, a rotatable plate 30 is pivotable on pivot pins 32 and 34 disposed in complemental apertures in the side faces of the scent device. As shown in FIGS. 2 and 3, the rotatable plate has a permanent magnet plate 36, magnetically or adhesively secured to the rotatable plate. The rotatable plate and magnet are provided to secure the scent device to a room vent of a heating and air conditioning system. Since the scent device is provided with a magnet it can be placed onto any metal vent opening by any unskilled or skilled person.

Since the fragrance block is provided with passages and the scent device is provided with vent openings in the front, the air from the blower will have little resistance from the scent device and will pass into the room with a minimum of resistance from the scent device.

If the blower vents are not made of metal, the rotatable plate could be fitted into a vent slot of the blower unit so that the scent device will be secured in place on the vent outlet.

It is clear that a scent device could be placed on the front of any vent outlet for adding a desired fragrance in any desired room. If it is desired not to have a fragrance in a particular room, the scent device would not be placed on a vent in that room. If one so chooses, a scent device could be secured to a return vent, in which case, the same fragrance would be directed into every vent outlet of the system.

In another embodiment of the invention shown in FIG. 7, the fragrance block would be inserted through an opening 38 in the side of the scent device. Rails or other similar supports are provided upon which the block is slid in order to secure the block in alignment with the opening.

It should be clear to one skilled in the art that the scent device need not have a side opening for reception of the fragrance block since the fragrance block could be fitted in the scent device within the open rear. Further, one could have a hinged vented door which would open for reception of the fragrance block. The manner in which the fragrance block is added to the scent device is not important. The important aspect is the feature by which the scent device can be secured to an outlet or return vent of a blower system.

Since the magnet is adhesively secured to the rotatable plate and the rotatable plate is pivotable on pivots in apertures of the housing, the housing and the rotatable plate can both be made of plastic. The magnet could be attachable to the rotatable plate by adhesive means or self-adhesively. Thus, the scent device could be made inexpensively. If the scent device is to be attached to a blower vent without use of the magnet, in this variation the rotatable plate would slide into a blower vent or louver opening for attaching or hooking the scent device to the blower vent.

As shown in FIG. 4, the hanging attachment 40 for the scent housing can be made of plastic or metal such that pivot end supports 42 on the body 44 are secured to the pivots 32 and 34 of the housing and the outer end 46 is bent at an angle of about 25°. Such a hanger can be inserted between the louvers of a standard vent and then by releasing the unit, the weight of the unit and gravity would hold it in place. This method would be best suited for ceiling and wall vents.

As shown in FIG. 5, this attachment uses two spring clips 48 having angular ends 50 mounted to the insides of the housing by incorporating small protrusions on the walls. Material preferably will be 0.01 gauge tempered wire that can be squeezed together then inserted between the louvers and released once inserted past the actual louver. The spring clip then expands and attaches itself into place. To remove, the clips are pressed together and withdrawn.

The foregoing relates to a preferred exemplary embodiment of the invention, it being understood that other variants and embodiments thereof are possible within the spirit and scope of the invention, the latter being defined by the appended claims.

I claim:

1. A scent device; said scent device includes a housing having a front face, upper and lower end faces, side faces and an open backside, said front face includes open vents, an opening in said housing through which a fragrance block is placed within said housing, and a pivotable plate secured to said side faces near a back edge of each of said side faces, a permanent magnet plate secured to said rotatable plate by which said housing can be secured to a vent opening of a blower system by said permanent magnet plate.

2. A scent device as set forth in claim 1, wherein; said open vents in said front face are parallel with said upper and lower end faces.

3. A scent device as set forth in claim 1, in which; one of said side faces includes an opening for reception of said fragrance block.

4. A scent device as set forth in claim 1, in which; said fragrance block includes passages therethrough extending from a backside to a front side, in which the front side of the passages aligns with said vents in said front face of said housing.

5. A scent device as set forth in claim 2, in which; said fragrance block includes passages therethrough extending from a backside to a front side, in which the front side of the passages aligns with said vents in said front face of said housing.

6. A scent device as set forth in claim 3, in which; said fragrance block includes passages therethrough extending from a backside to a front side, in which the front side of the passages aligns with said vents in said front face of said housing.

7. A scent device as set forth in claim 4, in which; said vents in said front face of said housing and said passages in said fragrance block are directed upwardly, and said rotatable plate is directed downward.

8. A scent device as set forth in claim 5, in which; said vents in said front face of said housing and said passages in said fragrance block are directed upwardly, and said rotatable plate is directed downward.

9. A scent device as set forth in claim 6, in which; said vents in said front face of said housing and said passages in said fragrance block are directed upwardly, and said rotatable plate is directed downward.

10. A scent device as set forth in claim 7, in which; said passages in said fragrance block are in alignment with at least some of the vents in said vent in said blower system, and with said vents in said front face of said housing.

11. A scent device as set forth in claim 8, in which; said passages in said fragrance block are in alignment with at least some of the vents in said vent in said blower system, and with said vents in said front face of said housing.

12. A scent device as set forth in claim 9, in which; said passages in said fragrance block are in alignment with at least some of the vents in said vent in said blower system, and with said vents in said front face of said housing.

13. A scent device as set forth in claim 1, in which said pivotable plate includes an angular end relative to said plate.

* * * * *